(12) United States Patent
Saiz

(10) Patent No.: US 9,993,321 B1
(45) Date of Patent: Jun. 12, 2018

(54) GAUGE SYSTEM FOR MEASURING UNDERBITE AND OVERBITE IN RUMINANTS

(71) Applicant: Juan Fernando Saiz, Sugar Land, TX (US)

(72) Inventor: Juan Fernando Saiz, Sugar Land, TX (US)

( * ) Notice: Subject to any disclaimer, the term of this patent is extended or adjusted under 35 U.S.C. 154(b) by 0 days. days.

(21) Appl. No.: 15/607,671

(22) Filed: May 29, 2017

(51) Int. Cl.
   *A61D 5/00* (2006.01)
   *A61C 19/04* (2006.01)
   *G01B 3/28* (2006.01)
   *A61C 7/36* (2006.01)

(52) U.S. Cl.
   CPC ............... *A61C 19/04* (2013.01); *G01B 3/28* (2013.01); *A61C 7/36* (2013.01)

(58) Field of Classification Search
   CPC ........................................................ A61D 5/00
   USPC ............................................................. 433/1
   See application file for complete search history.

(56) References Cited

U.S. PATENT DOCUMENTS

| 1,327,114 A | 1/1920 | Rhein |
| 4,997,368 A | 3/1991 | Mayer et al. |
| 5,044,951 A | 9/1991 | Sheridan |
| 5,676,544 A | 10/1997 | Urban |
| 6,430,830 B1 | 8/2002 | Segal |
| 8,444,415 B2 | 5/2013 | Thornton |
| 9,662,193 B1 * | 5/2017 | Saiz ........................ A61C 19/05 |
| 2008/0254400 A1 * | 10/2008 | Scherl ...................... A61C 3/00 433/1 |

* cited by examiner

*Primary Examiner* — Cris L Rodriguez
*Assistant Examiner* — Matthew Saunders
(74) *Attorney, Agent, or Firm* — Kenneth A. Roddy

(57) ABSTRACT

A gauge system for measuring underbite and overbite in ruminants includes a set of elongated generally S-shaped underbite gauge members and an underbite-overbite gauge member of unitary construction, each having an elongated handle portion configured to be gripped in the hand of a user, a first curved portion formed at one end of the handle portion and a second curved portion formed at the opposed end thereof, extending in vertically opposed relation to one another. The first and second curved portions of the underbite gauges and the first curved portion of the underbite-overbite gauge terminate in an underbite measuring tip of different thicknesses for measuring an underbite condition. The second curved portion of the underbite-overbite gauge has a flat rectangular overbite measuring tip that extends forward a distance from the second curved portion and is provided with a metric scale for measuring an overbite condition.

6 Claims, 2 Drawing Sheets

GAUGE SYSTEM FOR MEASURING UNDERBITE AND OVERBITE IN RUMINANTS

CROSS REFERENCE TO RELATED APPLICATION

This application is closely related to my U.S. patent application Ser. No. 15/144,815, filed on May 3, 2016.

BACKGROUND OF THE INVENTION

1. Field Of The Invention

This invention relates generally to instruments for determining jaw defects in animals, and more particularly to a gauge system for measuring underbite (brachygnathia superior) and overbite (brachygnatia inferior) in ruminants.

2. Background Art

All species of ruminants lack top incisors. All these animals have a tough dental pad below their top lip, sometimes referred to as the maxillary pad, instead of front teeth, and a huge gap between the dental pad (maxillary pad) and the back teeth Underbite (brachygnathia superior) and overbite (brachygnatia inferior) in ruminants are well known genetic jaw defects that develop as a result of several factors, including osteogenetic disorder, mechanical factors and heredity, and is characterized by failure of the premaxillary bone to grow to normal length and width.

A normal bite is known as the condition, when the mouth is closed in a bite position and the upper and lower jaw are perfectly aligned, the upper edge of the teeth crown (the part of a tooth external to the gum) is touching the front edge of the dental pad (maxillary pad) of the upper jaw.

Underbite (brachygnathia superior), also known as mandibular prognathism, although the first term is considered most correct, is a condition caused by failure of the premaxillary bone to grow to normal length and width. Prognathism refers to a protruding jaw. It is also called an extended chin. In this condition, when the mouth is closed in a bite position, the upper edge of the teeth crown is disposed forward of the front edge of the dental pad (maxillary pad) of the upper jaw.

Overbite (brachygnathia inferior), also known as mandibular brachygnathia, and commonly called parrot mouth prognathism, is a condition caused by failure of the anterior of the lower jaw forward of the premolars to grow to normal length, causing an abnormal shortness of the lower jaw. In this condition, when the mouth is closed in a bite position, the upper edge of the teeth crown is disposed rearward of the front edge, or anterior angle, of the dental pad (maxillary pad) of the upper jaw.

These jaw defects can lead to serious economic loses in bovine and sheep production systems, because it can seriously affect the grazing animal's ability to bite off foliage and have adequate nutrition.

Therefore it is important to be able identify and quantitatively measure these specific jaw defects in animals in order to select and eliminate those that have this problem, and also to have the ability to quantify the prevalence of underbite (brachygnathia superior) and overbite (brachygnatia inferior) in the animal population.

There are several patents directed toward gauge instruments for measuring various dental conditions. The following are several examples.

Rhein, U.S. Pat. No. 1,327,114, discloses an attachablepermanent depth gauge which is used with dental and medical instruments to for example, measure the length of a root canal. The gauge disclosed has two members, the first member being affixed or attached to the handle of the instrument and the second member being movable with respect to the first. Depth is measured by viewing an indicator which reflects the distance between the second member and the extremity of the instrument. The sliding gauge must be positioned to the zero point before the measurement is taken and the instrument must be removed from the patient's mouth in order to read the scale.

Mayer et al, U.S. Pat. No. 4,997,368, discloses an oral measuring insert device having biased top and bottom surfaces which can be directed into the mouth between the frontal upper and lower teeth to measure the opening of the mouth. The device is formed from a lightweight, disposable plastic having arcuate grooves positioned within the upper and lower surfaces providing detents for the teeth. Numerical indicia is disposed along the side of the insert to allow the examiner to quickly determine the degree of movement the mandible has undergone at maximum insertion. Various sizes of the insert may be manufactured and made available for different mouth sizes such as for example with young children, older children or adults.

Sheridan, U.S. Pat. No. 5,044,951, discloses a dental space and periodontal cavity measuring instrument for insertion in interdental or interproximal spaces between teeth and in periodontal cavities in both the upper and lower dental arches to determine the width of such spaces and the depth of the cavities, respectively, for appropriate treatment. The dental space and periodontal cavity measuring instrument has a centrally located handle provided with a pair of oppositely-extending single tips or multiple, elongated, graduated cylinders which terminate in graduated ends, for insertion in the interdental spaces and periodontal cavities. The calibrated cylinders and graduated ends may be extended in a straight line from the handle, or one or more cylinders in one or both of the calibrated and graduated tips may be angulated and the diameter of each cylinder may be indicated on the handle for size-identification purposes. The ends of the cylinder or stem tips may also be "waffled" with striations for ligature tucking purposes.

Urban, U.S. Pat. No. 5,676,544, discloses an instrument for subgingival scaling, root planing and maintenance of periodontal health. The instrument has an elongated body with a handle portion, a terminal shank portion, a working end, and a gauge. The terminal shank portion includes a base having a first portion, which is coaxial with the handle portion, and a second portion, which is angled from the first portion. The working end has a rear heel portion adjacent to the second portion and a front toe portion. Between the heel and toe there is a blade edge extending lengthwise. The gauge is arranged along the annular surface of the second portion of the terminal shank. In order to measure the periodontal health of the patient on whom the instrument is being used, the instrument is inserted into the periodontal space between the tooth and the gum. The depth of the periodontal space is determined by reading the marking on the gauge which meets the gumline.

Segal, U.S. Pat. No. 6,430,830 discloses a dental measuring device can be used to measure the separation of reference positions on a patient's upper and lower jaws to assist in the construction of dentures. The device has two elements which slide longitudinally relative to each other with a pointer on one and a scale on the other. The elements have projecting arms. The sliding elements can be reversed so that in one position the arms point in the same direction for measuring the separation of specific points on the patient's nose and chin, and in a second position the arms point in opposite directions for positioning beneath the patient's nose and chin.

Thornton, U.S. Pat. No. 8,444,415 discloses a dental measurement apparatus for measuring mandibular position that includes a first slide operable to adjustably couple to a second slide, such that the second slide is operable to travel in a direction substantially parallel to a long axis of the first slide, and an indicator configured to indicate a location of the second slide relative to the first slide in the direction substantially parallel to the long axis of the first slide. The apparatus further includes an adjustment mechanism coupled to the first slide and the second slide, the adjustment mechanism configured to adjust the distance between the first slide and the second slide in a direction substantially orthogonal to the long axis of the first slide.

My U.S. patent application Ser. No. 15/144,815, discloses a gauge system for measuring underbite and overbite in ruminants that includes a handle having a spring biased retainer pivotally mounted thereon and a head portion at a front end having a tip receiving aperture, a set of interchangeable underbite measuring tips for use with cattle, a set of interchangeable underbite measuring tips for use with sheep, and a overbite measuring tip. The rear portion of the tip retainer is depressed by a user's thumb to pivot the front portion of the tip retainer upwardly to an open position and expose the tip receiving aperture for insertion or removal of a selected underbite measuring tip, or the overbite measuring tip, and thereafter removing the thumb allows the front portion of the tip retainer member to be lowered under spring pressure to the closed position and retain the selected underbite measuring tip, or the overbite tip in the aperture.

SUMMARY OF THE INVENTION

The present invention overcomes the aforementioned problems and is distinguished over the prior art in general, and these patents in particular, by a gauge system for measuring underbite (brachygnathia superior) and overbite (brachygnathia inferior) in ruminants. The gauge system for measuring underbite and overbite in ruminants includes a set of elongated generally S-shaped underbite gauge members and an underbite-overbite gauge member of unitary construction, each having an elongated handle portion configured to be gripped in the hand of a user, a first curved portion formed at one end of the handle portion and a second curved portion formed at the opposed end thereof, extending in vertically opposed relation to one another. The first and second curved portions of the underbite gauges and the first curved portion of the underbite-overbite gauge terminate in an underbite measuring tip of different thicknesses for measuring an underbite condition. The second curved portion of the underbite-overbite gauge has a flat rectangular overbite measuring tip that extends forward a distance from the second curved portion and is provided with a metric scale for measuring an overbite condition.

In a preferred embodiment the underbite measuring tips are of a flat a flat rectangular configuration each having has a different thickness of a standard unit of measurement that ranges from 2 mm to 8 mm, respectively. The forwardly extending overbite measuring tip has top and bottom surface and lateral sides has a metric scale divided into millimeters with major markings at 5 mm, 10 mm, 15 mm, and 20 mm beginning at the outer end.

DETAILED DESCRIPTION OF THE INVENTION

Figure 1:
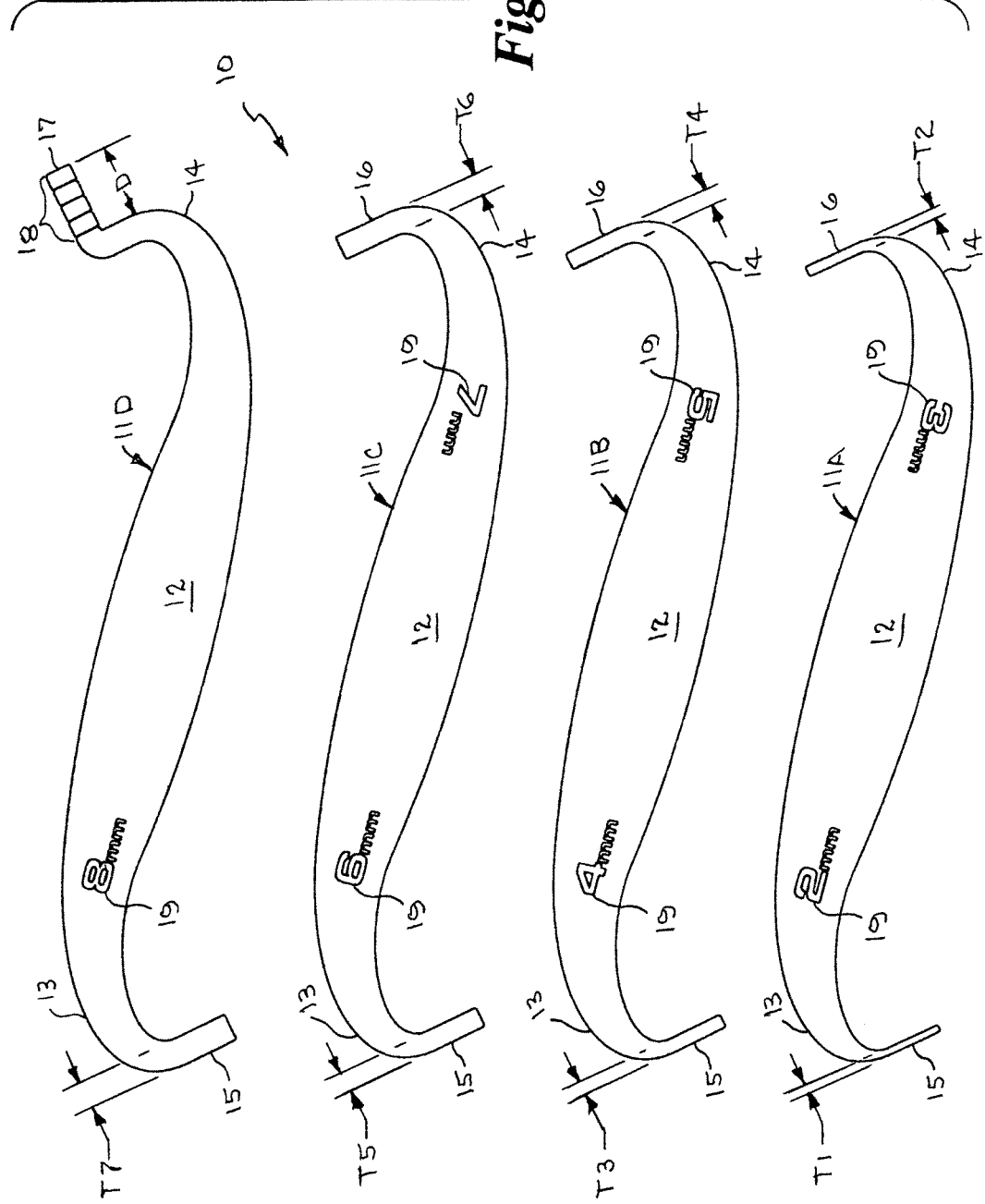
FIG. 1 is a side elevation view of the gauge system for measuring underbite (brachygnathia superior) and overbite (brachygnatia inferior) in ruminants, in accordance with the present invention, the opposite sides being mirror images thereof.
Figure 2:
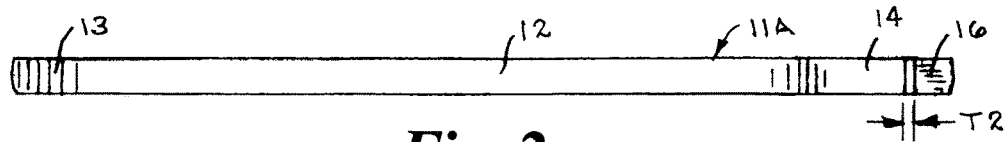
FIGS. 2 and 3 are a top plan view, and a bottom plan view, respectively, of a first one the underbite measuring gauge members.
Figure 3:
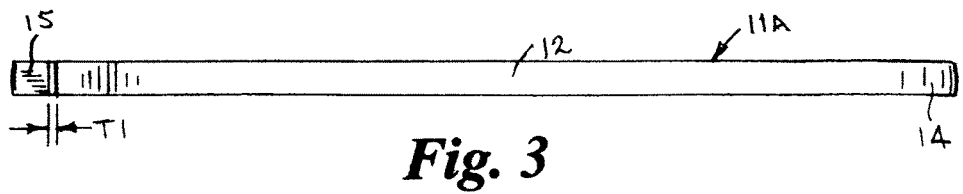
Figure 4:
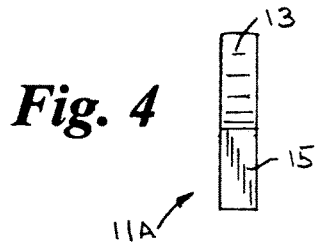
FIGS. 4 and 5 are a first end view, and a second end view of the first one of the underbite measuring gauge members, the other underbite measuring gauge members being essentially the same as shown in FIGS. 2 through 5, except for the thickness of the flat rectangular underbite measuring tips at opposed ends.
Figure 5:
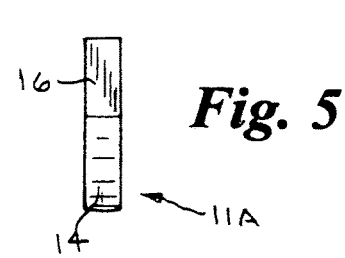
Figure 6:
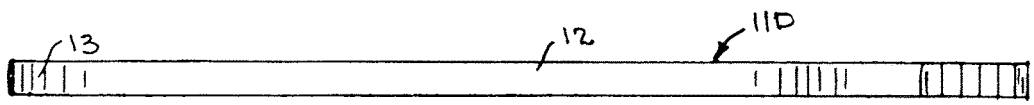
FIGS. 6 and 7 are a top plan view, and a bottom plan view, respectively, of the underbite-overbite measuring gauge member.
Figure 7:
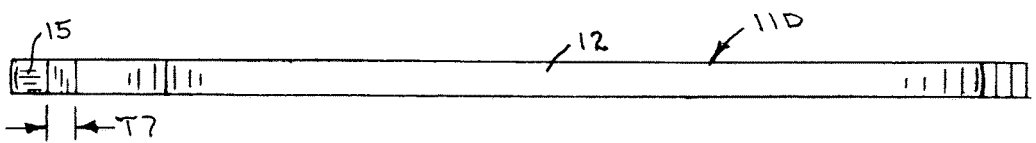
Figure 8:
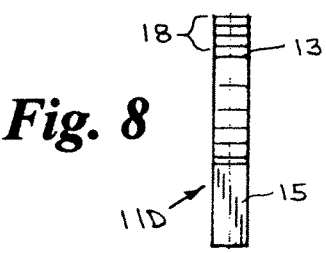
FIGS. 8 and 9 are a first end view, and a second end view of the underbite-overbite measuring gauge member.
Figure 9:
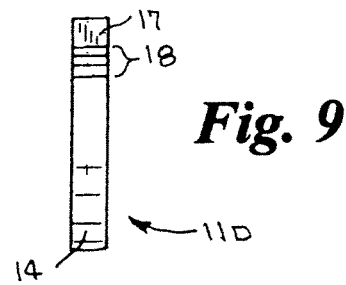

Referring to the drawings by numerals of reference, there is shown in FIG. 1, the components of a gauge system 10 for measuring underbite (brachygnathia superior) and overbite (brachygnatia inferior) in ruminants, such as cows and sheep.

The gauge system 10 includes a plurality of elongated generally S-shaped underbite measuring gauge members 11A, 11B, 11C, and an underbite-overbite measuring gauge member 11D, each of unitary construction.

Referring additionally to FIGS. 2-5, each of the underbite measuring gauge members 11A, 11B, and 11C, has three main sections; a central elongate generally rectangular handle portion 12 which is configured to be gripped in the right or left hand of a user, a first curved portion 13 integrally formed at one end of the handle portion, and a second curved portion 14 integrally formed at the opposed end. The curved portions 13 and 14 extend in vertically opposed relation to one another.

Each of the opposed curved portions 13 and 14 of the underbite measuring gauge members 11A, 11B and 11C terminate in a respective integrally formed flat rectangular underbite measuring tip 15 and 16. Each of the flat rectangular underbite measuring tips 15 and 16 of the underbite measuring gauge members 11A, 11B, and 11C, are of a different thickness T1, T2, T3, T4, T5, and T6 of a standard unit of measurement that ranges from 2 mm to 6 mm, respectively.

Referring now to FIGS. 1, 6, 7, 8, and 9, the underbite-overbite measuring gauge member 11D also has a generally S-shaped configuration, with a central elongate generally rectangular handle portion 12 which is configured to be gripped in the right or left hand of a user, a first curved portion 13 integrally formed at one end of the handle portion, and a second curved portion 14 integrally formed at the opposed end. The first and second curved portions 13 and 14 extend in vertically opposed relation to one another. The first curved portion of the underbite-overbite measuring gauge member 11D terminates in an integrally formed flat rectangular underbite measuring tip 15, which has a thickness T7 of a standard unit of measurement that is different from the previously described underbite measuring gauges, for example 8 mm.

The second curved portion 14 of the underbite-overbite measuring gauge member 11D has an integrally formed flat rectangular overbite measuring tip 17 that extends perpendicularly forward a distance relative to a plane tangent to the convex periphery of the second curved portion and terminates a distance D therefrom. The top and bottom surfaces and lateral sides of the overbite measuring tip 17 is provided with a metric scale 18 divided into millimeters with major divisional lines at 5 mm, 10 mm, 15 mm, and 20 mm beginning at the outer end thereof.

As described above, the underbite measuring tips 15 and 16 of the underbite measuring gauge members 11A, 11B, 11C, and the underbite-overbite measuring gauge member 11D are of a different thickness T1, T2, T3, T4, T5, T6, and T7.

Each side of the handle portion 12 of the handle portion 12 the gauge members 11A, 11B, 11C, and 11D may be provided with a numeral 19 closely adjacent to the curved portion that corresponds to the respective unit of measurement. All of the gauge members may be of the same width, such as for example 10 mm, but not limited thereto. The vertical thickness of the forwardly extending rectangular overbite measuring tip 17 may be about 7.6 mm, for example but not limited thereto.

Table 1 below illustrates an example of a numbering system that may be utilized for easily and quickly identifying the respective underbite measuring tips 15 and 16.

TABLE 1

| DIMENSION (See Drawing) | UNDERBITE TIP NUMERAL | THICKNESS MM | THICKNESS INCH |
|---|---|---|---|
| T1 | 2 mm | 2 | .08 |
| T2 | 3 mm | 3 | .12 |
| T3 | 4 mm | 4 | .16 |
| T4 | 5 mm | 5 | .20 |
| T5 | 6 mm | 6 | .24 |
| T6 | 7 mm | 7 | .28 |
| T7 | 8 mm | 8 | .32 |

OPERATION

The above described gauge members are preferably provided as a kit ready to be used to quickly and accurately measure the underbite or overbite condition of the animal.

It is recommended that at least two people be present in order to make a proper measurement of the animal's bite; one person that holds and opens the animal's mouth, and another person that places the tool in the animal's mouth and measures the bite.

The animal is placed in a location where its head can be safely held still in a secure manner, not only for the animal, but also for the safety of the person holding the animal and the person that is using the measuring tool.

A muzzle is placed on the animal's head to immobilize and prevent the animal from moving its head.

After the animal's head is immobilized and with its mouth in a closed biting position, one person places both hands with the fingers facing up and the palm in front of the animal's lips, then, using their the fingers to open the lips, to make sure the animal stays in a biting position with the mouth closed.

Normal Bite Condition

With the animal's lips open and its mouth closed in the bite position, if it is seen that the upper and lower jaw are perfectly aligned, the edge of the teeth or crown should be touching the front edge of the dental pad (maxillary pad) in the upper jaw of the animal, this is considered to be a normal bite condition.

Underbite Condition

If the crown of the lower teeth is not touching the dental pad (maxillary pad) in the mouth closed, bite position, it means that the animal has an unusual bite or an underbite, and in which case the underbite measuring tips are is used to measure the distance between the back of the teeth and the gum at the top of the edge of the dental pad (maxillary pad).

This is accomplished, with the animal's mouth closed in the bite position and the lips open, by gripping the handle portion 12 of a selected underbite measuring gauge member such that the flat rectangular underbite measuring tip 15 or 16 at one end is facing downward and placing the underbite measuring tip in the space between the teeth and the dental pad (maxillary pad). In order to achieve an exact measurement, the thickness of the flat rectangular measuring leg of the underbite measuring tip 15 or 16 has to fit perfectly in the space between the back of the teeth and the front edge of the dental pad (maxillary pad). Thus, it may require inverting and swapping ends of the gauge member or selecting another underbite measuring gauge member until the one having the proper tip thickness (i.e., from 2 mm to 8 mm) is found to perfectly fit the space between the back of the teeth and the front edge of the dental pad (maxillary pad). This allows the exact measure according to the thickness (millimeter number) of the tip used which can be easily and quickly determined by reading the numeral closely adjacent to the curved portion of the gauge.

Overbite Condition

If the crown of the lower teeth touches the dental pad (maxillary pad) behind the anterior angle of the dental pad, it means that the animal has an overbite, and in which case, the underbite-overbite gauge member 11D having the overbite measuring tip 17 is used to measure the space between the lower teeth and the anterior angle of the dental pad. This is accomplished, with the animal's mouth closed in the bite position and the lips open, by placing the overbite measuring tip 17 in the front part of the teeth with the rectangular measuring tip portion extending to the anterior angle of the dental pad (maxillary pad), and reading the scale 18 on the tip to determine the distance between the teeth and how far they are from the dental the dental pad (maxillary pad).

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A gauge system for measuring underbite (brachygnathia superior) and overbite (brachygnatia inferior) in ruminants, comprising:
   a set of elongated generally S-shaped gauge members including a plurality of underbite measuring gauge members, and an underbite-overbite measuring gauge member of unitary construction;
   each of said underbite measuring gauge members and said underbite-overbite measuring gauge member having an elongated handle portion configured to be gripped in the hand of a user, a first curved portion formed at one end of the handle portion and a second curved portion formed at the opposed end thereof, extending in vertically opposed relation to one another;

each of said first and second curved portions of said underbite gauges and said first curved portion of said underbite-overbite measuring gauge member terminating flat rectangular underbite measuring tip of different thicknesses, respectively, for measuring an underbite condition;

said second curved portion of said underbite-overbite measuring gauge member having a flat rectangular overbite measuring tip that extends forward a distance from said second curved portion and provided with a metric scale for measuring an overbite condition.

2. The gauge system according to claim 1, wherein said flat rectangular underbite measuring tips each has a different thickness of a standard unit of measurement that ranges from 2 mm to 8 mm, respectively.

3. The gauge system according to claim 1, wherein said metric scale of said forwardly extending overbite measuring tip extends across top and bottom surfaces and lateral sides thereof which is divided into millimeters with major markings at 5 mm, 10 mm, 15 mm, and 20 mm beginning at an outer end thereof.

4. The gauge system according to claim 1, further comprising:

a numeral on each side of said handle portion of each of said underbite measuring gauges closely adjacent to said first and second curved portions, that corresponds to the respective unit of measurement of the thickness of the respective underbite measuring tip; and a numeral on each side of said handle portion of underbite-overbite measuring gauge closely adjacent to said first curved portion, that corresponds to the respective unit of measurement of the thickness of the underbite measuring tip.

5. A gauge system for measuring underbite (brachygnathia superior) and overbite (brachygnatia inferior) in ruminants, comprising:

a set of gauge members including a plurality of underbite measuring gauge members, and an underbite-overbite measuring gauge member;

each of said underbite measuring gauge members and said underbite-overbite measuring gauge member having a generally S-shaped configuration of unitary construction, with a central elongate generally rectangular handle portion configured to be gripped in the right or left hand of a user, a first curved portion integrally formed at one end of the handle portion and a second curved portion integrally formed at the opposed end thereof, said curved portions extending in vertically opposed relation to one another, and each of said opposed curved portions terminating in an integrally formed flat rectangular underbite measuring tip, each said underbite tip having a different thickness of a standard unit of measurement that ranges from 2 mm to 6 mm, respectively; and said underbite-overbite measuring gauge having a generally S-shaped configuration of unitary construction, with a central elongate generally rectangular handle portion configured to be gripped in the right or left hand of a user, a first curved portion integrally formed at one end of the handle portion and a second curved portion integrally formed at the opposed end thereof, said curved portions extending in vertically opposed relation to one another, said first curved portion terminating in an integrally formed flat rectangular underbite measuring tip having a thickness of 8 mm and said second curved portion having an integrally formed flat rectangular overbite measuring tip that extends perpendicularly forward a distance relative to a plane tangent to the convex periphery of said second curved portion and terminates a distance therefrom, and the top and bottom surfaces and lateral sides of said overbite measuring tip provided with a metric scale divided into millimeters with major divisional lines at 5 mm, 10 mm, 15 mm, and 20 mm beginning at the outer end thereof.

6. The gauge system according to claim 5, further comprising:

a numeral on each side of said handle portion of each of said underbite measuring gauges closely adjacent to said first and second curved portions, that corresponds to the respective unit of measurement of the thickness of the respective underbite measuring tip; and a numeral on each side of said handle portion of underbite-overbite measuring gauge closely adjacent to said first curved portion, that corresponds to the respective unit of measurement of the thickness of the underbite measuring tip.

* * * * *